United States Patent [19]

Busse

[11] 4,281,709
[45] Aug. 4, 1981

[54] THERMAL HEAT PUMP

[75] Inventor: Claus A. O. Busse, Arolo di Leggiuno, Italy

[73] Assignee: European Atomic Energy Community-EURATOM, Plateau du Kirchberg, Luxembourg

[21] Appl. No.: 937,373

[22] Filed: Aug. 28, 1978

[30] Foreign Application Priority Data

Sep. 2, 1977 [DE] Fed. Rep. of Germany ....... 2739689

[51] Int. Cl.³ .......................................... F28D 15/00
[52] U.S. Cl. ................. 165/104.22; 62/500; 165/104.26
[58] Field of Search .......................... 165/105; 62/500

[56] References Cited

U.S. PATENT DOCUMENTS

| 3,532,159 | 10/1970 | Hammitt et al. | 165/105 |
| 3,568,762 | 3/1971 | Harbaugh | 165/105 |
| 3,621,667 | 11/1971 | Mokadam | 62/500 X |

FOREIGN PATENT DOCUMENTS 549674  6/1977  U.S.S.R. .................................. 165/105

Primary Examiner—Albert W. Davis
Attorney, Agent, or Firm—Sughrue, Rothwell, Mion, Zinn and Macpeak

[57] ABSTRACT

The present invention relates to a thermal heat pump consisting of a heat pipe in which the vapor passage between the heat transfer zone to the heat supply and the heat transfer zone to the heat removal section has a cross section which varies across its length. The variable cross-sectional vapor passage first increases and then decreases the rate of vapor flow, and a further heat transfer zone with either heat supply or removal is located in the area of increased vapor velocity. The cross-sectional variation of the vapor passage in the heat pipe between the two outermost heat transfer zones is advantageously brought about by a displacement body arranged internally of the heat pipe with a particular surface contour.

9 Claims, 5 Drawing Figures

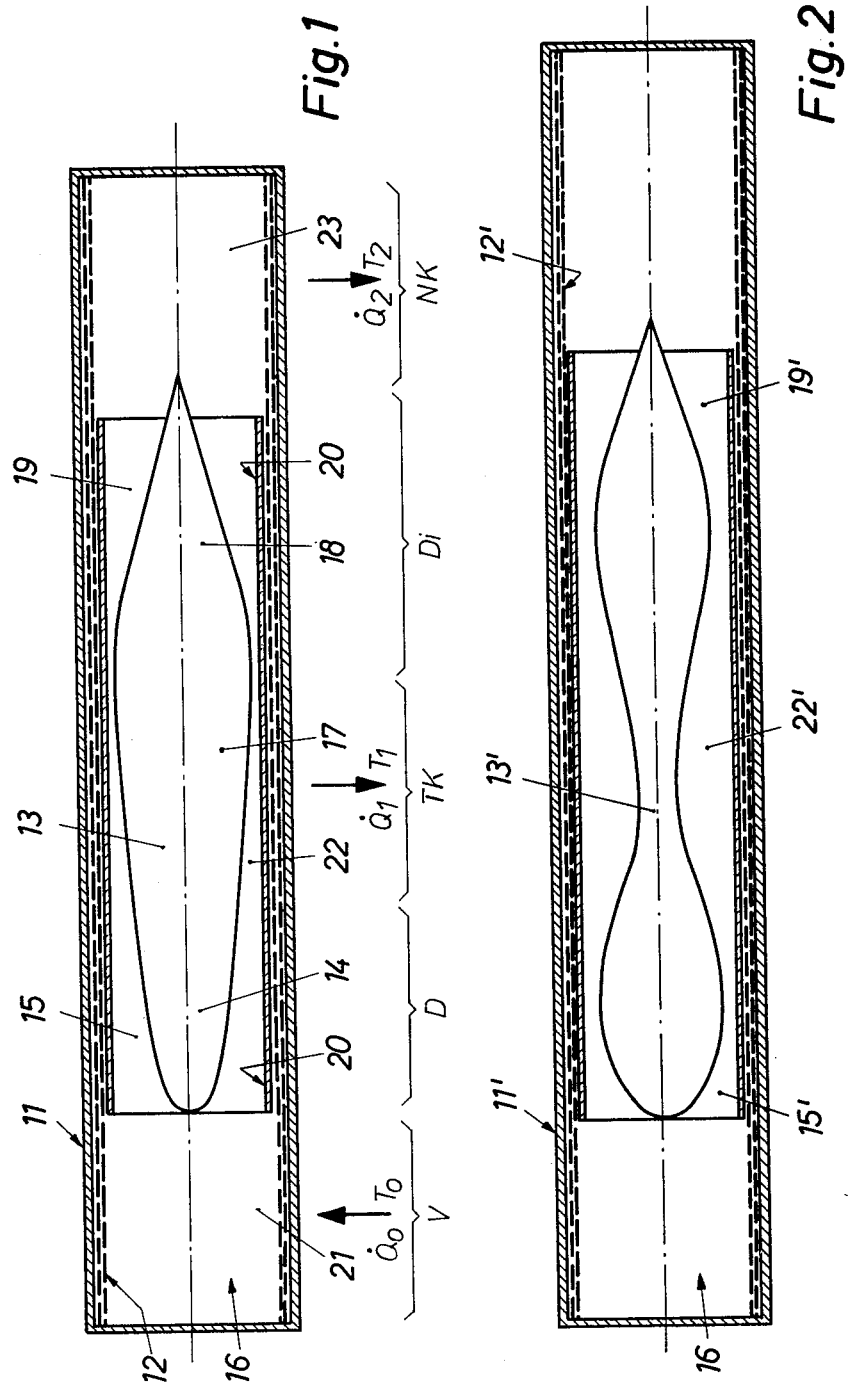

U.S. Patent    Aug. 4, 1981    Sheet 2 of 2    4,281,709
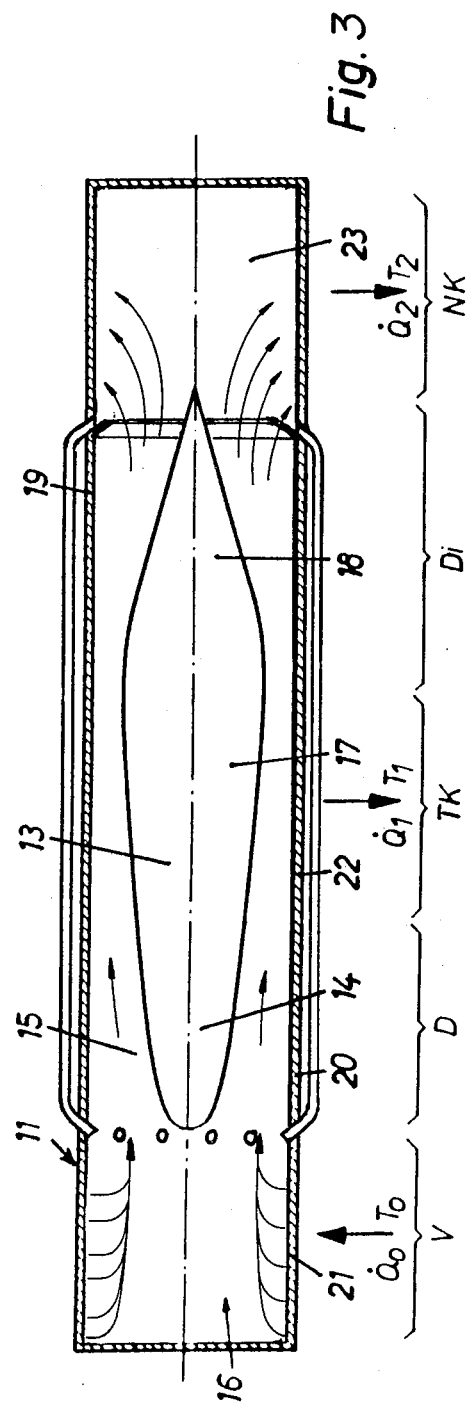
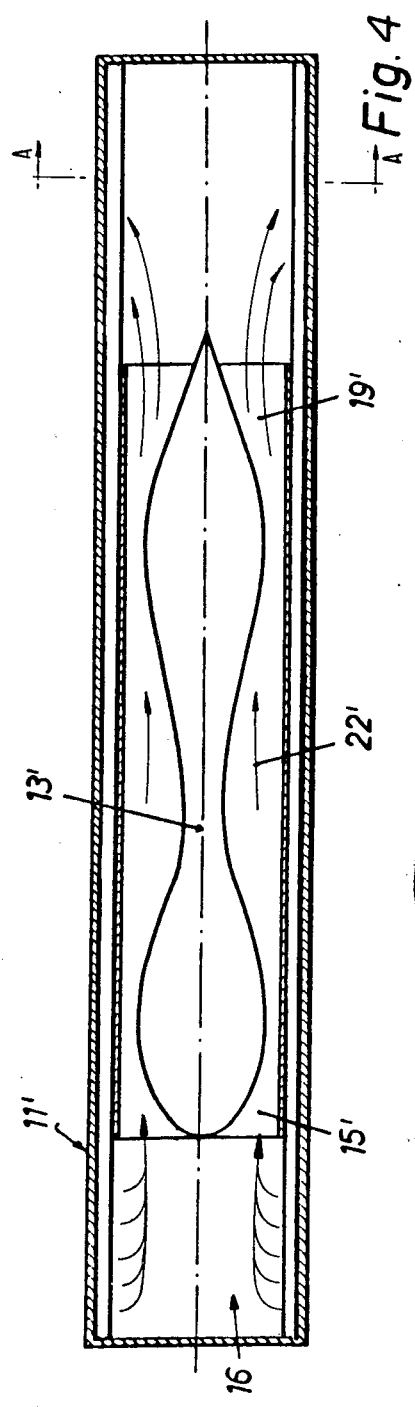
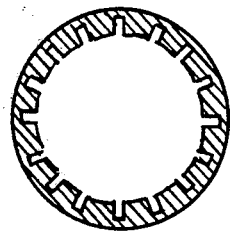

THERMAL HEAT PUMP

A compensation process has to be used in order to raise heat from a lower temperature level to a higher temperature level so that the total entropy of all substances involved does not decrease. A compensation process with expenditure of mechanical work is used with the hitherto generally common heat pumps; the expenditure of mechanical work is based on the operation of a compressor.

Deliberations have lead to also operating the compensation process through heat, and in such a way that heat is fed at a mean temperature of $T_o$ and that this heat is released again at a lower temperature of $T_1$ as well as at a higher temperature of $T_2$. Such a thermal heat pump which is the subject matter of the invention is thus operated by the temperature drop between $T_o$ and $T_1$, wherein the thermal efficiency can be calculated from the following equation:

$$\eta = \frac{\dot{Q}_2}{\dot{Q}_0} \cdot \frac{1 - \frac{T_1}{T_0}}{1 - \frac{T_1}{T_2}}$$

wherein $\dot{Q}_o$ is the taken up heat flow and $\dot{Q}_2$ is the useful heat flow at the temperature $T_2$.

Such operating thermal heat pumps are of great interest for the exploitation of temperature differences caused by solarization, in particular for the purpose of heating water or other media for heating purposes, for the supply of warm water and the like.

The thermal heat pump constructed according to the invention consists of a heat pipe in which the vapor passage located between the heat transfer zone to the heat supply and the heat transfer zone to the heat removal has a cross section which varies across its length and which increases the velocity of the vapor flow to begin with and then decreases it, and wherein a further heat transfer zone with heat supply or heat removal is located in the area of the increased vapor velocity.

The thermal heat pump according to the embodiment of the subject matter of the invention consists of a heat pipe, in the vapor passage of which a displacement body is arranged between the heat supply or evaporating area and the heat removal or useful condenser area, which alters the vapor velocity.

The area in front of the displacement body is the evaporating area "V" into which the heat flow $\dot{Q}_o$ is supplied at a mean temperature $T_o$. The area roughly in the middle of the displacement body is the driving condenser area "TK" in which part of the vapor is condensed at a mean temperature $T_1$ which is less than the temperature $T_o$, wherein the heat flow $\dot{Q}_1$ is removed. Behind the displacement body is the useful condenser area "NK" in which the remaining vapor is condensed at a mean temperature $T_2$ and the useful heat flow $\dot{Q}_2$ is removed. The condensate resulting in the driving condenser area "TK" and in the useful condenser area "NK" is returned to the evaporating area "V" by way of a suitable, per se known, capillary structure lining the inner wall of the heat pipe in the usual manner.

The operating method of the aforementioned embodiment of the heat pump according to the invention can also be altered in such a way that it is thermodynamically reversed which results in that the driving condenser area then becomes a second evaporating area. Thus a relatively large amount of heat can be transported from a low to a medium temperature.

Further features of the thermal pump according to the invention can be seen from the following description of the preferred practical examples as well as from the sub claims.

BRIEF DESCRIPTION OF THE DRAWINGS

FIGS. 1 and 2 illustrate a thermic vapor ejector heat pump in schematic presentation, the FIG. 1 construction being suitable for subsonic vapor flow and the construction of FIG. 2 being suitable for supersonic vapor flow.

FIGS. 3 and 4 are views similar to those in FIGS. 1 and 2, depicting alternatives to the capillary condensate return structure depicted in FIGS. 1 and 2, and FIG. 5, is a cross-sectional view taken along the lines A—A in FIG. 4.

The heat pump for subsonic flow according to FIG. 1 consists of a heat pipe 11 on the inner wall of which a capillary structure 12 is arranged. The displacement body 13 is arranged in the interior of the heat pipe 11 in equal distance from the capillary structure 12, the front area 14 of which is formed in such a way that a jet 15 is formed between the displacement body and the capillary structure 12, in which the cross section of the vapor passage 16 is reduced. Behind the jet 15 the cross section of the vapor passage 16 between the center part 17 of the displacement body 13 and the capillary structure 12 is slightly reduced due to the form of the displacement body. A portion of the vapor is condensed in this area through cooling. The herewith coherent pressure and temperature increase is practically eliminated as a result of the reduction in the cross section of the vapor passage. The rear portion 18 of the displacement body 13 is cone-shaped so that the cross section of the vapor passage 16 widens in accordance with the aperture angle of the cone and forms a diffuser 19.

In view of the high pressure differences along the heat pump the capillary structure 12 is advantageously equipped with a thin-walled cover 20 in the area of the displacement body 13, which has to be connected to the capillary structure or the pipe of the heat pipe 11 in a sufficiently tight manner so as to prevent lifting due to partial vacuum. It has the purpose of driving the resulting condensate by way of the shearing effect of the vapor flow on the cover into the useful condenser zone to begin with, in which the pressure is higher than in the evaporating zone where it is still higher than in the driving condenser zone.

The thermal heat pump with supersonic flow according to FIG. 2 has basically the same structure as the one according to FIG. 1. The essential difference consists in that the displacement body 13' is formed in such a way that the jet 15' as well as the diffuser 19' show a convergent and a divergent portion, wherein the transition from the subsonic to the supersonic flow occurs at the narrowest part.

The mode of operation of the thermal heat pump is as follows:

The heat flow $\dot{Q}_o$ is fed to the vaporizer 21 at a mean temperature $T_o$. In the jet 15 which is formed by the front portion of the displacement body 13, the cross section of the vapor passage 16 is reduced, causing the vapor to expand. Herewith it cools down and partially condenses in the following driving condenser 22 at a mean temperature $T_1 < T_o$, wherein the heat flow $\dot{Q}_1$ is removed. The kinetic energy of the condensed vapor remains in the remaining vapor so that the specific kinetic energy thereof increases. The compression with corresponding temperature increase which usually occurs in a condenser in the downstream direction of the flow is prevented by the expansion of the vapor in the driving condenser 22, that being through corresponding reduction of the vapor passage cross section. In the following diffuser 19 the vapor is compressed through the expansion of the vapor passage cross section, wherein its kinetic energy is converted into pressure and the temperature of the vapor increases. The remaining vapor is condensed at a mean temperature $T_2$ in the useful condenser 23 following the diffuser 19, wherein the useful heat flow $\dot{Q}_2$ is given off. Higher temperatures can be obtained in the useful condenser 23 than in the vaporizer 21 as the specific kinetic energy of the vapor is higher when entering the diffuser 19 than when leaving the jet 15.

The condensate resulting in the driving condenser 22 and in the useful condenser 23 is lead back to the vaporizer 21 via the capillary structure 12 on the inner wall of the heat pipe 11.

The following dimensioning is tp be provided for a thermal heat pump with a heat input of $\dot{Q}_o = 1$ kw:

Heat carrier: $H_2O$
Wall material: Cu
Vapor passage cross section in vaporizer: 6.7 cm$^2$
Vapor passage cross section at the jet exit: 1.9 cm$^2$
Vapor passage cross section at the driving condenser exit: 1.0 cm$^2$
Mach number at the jet exit: 0.69
Mach number at the driving condenser exit: 0.97

The temperature differences which can be obtained with subsonic flow amount to only a few percent of the absolute temperature as the above data reveal. Greater temperature differences can be obtained with thermal heat pumps with supersonic flow.

An embodiment of the thermal heat pump is also possible, in which a subsonic jet according to FIG. 1 is used, the transition to supersonic flow occurs in the driving condenser and a supersonic diffuser according to FIG. 2 is used subsequently.

The condensate is lead back in a known manner to the vaporizer along the inner wall of the heat pipe by way of the capillary structure. The return occurs essentially on the basis of the capillary forces which can be enforced by the gravity as the case may be. However, it is also possible, as mentioned, to additionally utilize the higher pressure in the useful condenser for driving the fluid flow in the capillary structure.

Furthermore it is possible to replace the covered portion of the capillary structure in the interior of the heat pipe with one or more tubes, ducts or the like which can also be arranged on the outer side of the heat pipe as the case may be, in order to influence the vapor flow as little as possible.

The displacement body in the interior of the heat pipe is expediently placed on an axially arranged supporting member which is preferrably thermally insulated or which consists of a material which does not easily conduct heat.

Furthermore, it can be advantageous to arrange roughly cone-shaped displacement bodies in the useful condensing zone and possibly also in the evaporating zone as the case may be, the base surfaces of which face the front surfaces of the heat pipe.

It is advantageous to use a cylindrical heat pipe with capillary structure lining and cover, in which a displacement body with the required cross section form is located. A displacement body can of course also be used which has at least cylindrical construction in its middle portion so that the cross sections of the vaporpassage in the various areas are determined by the walls of the heat pipe. This solution however is less advantageous. The described and presented embodiments have essential advantages as losses by layer separation in the driving condenser and diffuser as well as temperature losses through a larger heat transfer surface in the driving condenser can be prevented; moreover the constructive form and the productability is far simpler as well as more stable.

With a practical example of application, for the purpose of optimum utilization of solar energy, the heat pipe could be arranged in such a way that the amount of heat $\dot{Q}_o$ which is supplied to the thermal heat pump in the evaporating area originates from sun rays; the amount of heat $\dot{Q}_1$ is removed by a cooling agent, for example in an area which is not exposed to the sun rays, and the amount of heat $\dot{Q}_2$ resulting in the useful condenser could be utilized for the heating of a useful medium.

The thermal heat pump according to the invention has the advantage of slighter losses, of a small and simple construction as well as being maintenance-free, resulting in low initial and operating costs.

Finally the variable design of the cross section of the vapor passage of the heat pipe can also be obtained in that the displacement body is omitted and the heat pipe is cross sectionally variably constructed according to the required duct configuration instead, and thus obtain the same flow effect as with the aforementioned embodiments.

I claim:

1. Thermal heat pump, characterized by a heat pipe in which the vapor passage located between the heat transfer zone to the heat supply and the heat transfer zone to the heat removal has a cross section which varies across its length and which increases the velocity of the vapor flow to begin with and then decreases it and that a further heat transfer zone with heat removal is located in the area of the increased vapor velocity.

2. Thermal heat pump according to claim 1, characterized in that a displacement body is arranged in the vapor passage of the heat pipe between the evaporating area and the useful condenser area, which alters the vapor velocity.

3. Thermal heat pump according to claim 2, characterized in that the cross sectional surface of the vapor passage is reduced in a jet-like manner downstream of the flow along the front portion of the displacement body, that it is slightly reduced along the middle portion of the displacement body and that it is widened in a diffuser-like manner along the rear portion of the displacement body, wherein the cross sectional alterations of the vapor passage are dimensioned in such a way that the Mach number of the vapor flow lies below 1,0 at each point.

4. Thermal heat pump according to claim 2, characterized in that the jet and the diffuser each consist of a convergent and a divergent part, wherein the cross sectional alterations of the vapor passage are dimensioned in such a way that the Mach number of the vapor which enters into the area of increased vapor velocity (TK) lies above 1,0.

5. Thermal heat pump according to claim 4, characterized in that the jet is a subsonic jet, that the cross sectional conditions in the vapor passage are dimensioned in such a way that the transition from the subsonic to the supersonic flow occurs in the area of the increased vapor velocity (TK) and that the diffuser (Di) is a supersonic diffuser.

6. Thermal heat pump according to claim 2 characterized in that the capillary structure along the inner wall of the heat pipe is provided with a cover against the vapor passage roughly over the length of the displacement body.

7. Thermal heat pump according to claim 2 characterized in that the capillary structure is totally or partially replaced roughly in the area of the displacement body by tubes, ducts and the like, which are arranged inside or outside of the pipe wall of the heat pipe.

8. Thermal heat pump according to claim 2 characterized in that the displacement body is placed on a thermally insulated axial support member.

9. Thermal heat pump according to claim 2 characterized in that appoximately cone-shaped displacement bodies are arranged in the useful condenser area (NK) and in the evaporating area (V) as the case may be, the base surfaces of which face the front surfaces of the heat pipe.

* * * * *